United States Patent [19]

Torii et al.

[11] 4,379,032

[45] Apr. 5, 1983

[54] PROCESS FOR PREPARING OXAZOLINEAZETIDINONE DERIVATIVES

[75] Inventors: Sigeru Torii, Akaiwa; Hideo Tanaka, Okayama; Junzo Nokami, Okayama; Takashi Shiroi, Okayama; Norio Saito, Itano; Michio Sasaoka, Okayama, all of Japan

[73] Assignee: Otsuka Kagaku Yakuhin Kabushiki Kaisha, Osaka, Japan

[21] Appl. No.: 407,134

[22] Filed: Aug. 9, 1982

[51] Int. Cl.³ .............................................. C25C 1/00
[52] U.S. Cl. ................................................. 204/59 R
[58] Field of Search .................................... 204/59 R

[56] References Cited

PUBLICATIONS

S. Uyeo et al. J. Am. Chem. Soc. 101 4403 (1979).
Barton et al. J. Chem. Soc. (c) 3540 (1971).
J. Stoodley et al. J. Chem. Soc., Perkin I, 181, (1978).

*Primary Examiner*—John F. Niebling
*Attorney, Agent, or Firm*—Larson and Taylor

[57] ABSTRACT

This invention provides a process for preparing an oxazolineazetidinone derivative represented by the formula

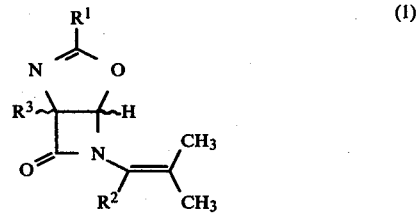

(wherein $R^1$ represents hydrogen atom, alkyl group, alkenyl group, substituted or unsubstituted aralkyl group, substituted or unsubstituted aryl group, or substituted or unsubstituted aryloxymethyl group, $R^2$ represents free or protected carboxyl group and $R^3$ represents hydrogen atom or methoxy group) from a penicillin derivative represented by the formula

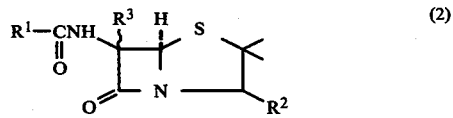

wherein $R^1$, $R^2$ and $R_3$ are as defined above.

10 Claims, No Drawings

PROCESS FOR PREPARING OXAZOLINEAZETIDINONE DERIVATIVES

This invention relates to a novel process for preparing an oxazolineazetidinone derivative and particularly to an improved process for preparing an oxazolineazetidinone derivative represented by the formula

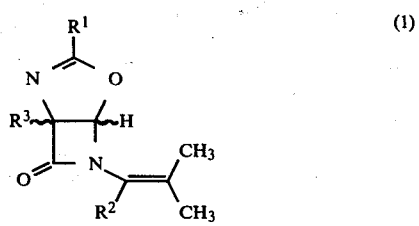

(wherein $R^1$ represents hydrogen atom, alkyl group, alkenyl group, substituted or unsubstituted aralkyl group, substituted or unsubstituted aryl group, or substituted or unsubstituted aryloxymethyl group, $R^2$ represents free or protected carboxyl group and $R^3$ represents hydrogen atom or methoxy group) from a penicillin derivative represented by the formula

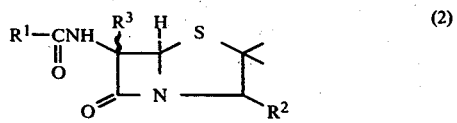

wherein $R^1$, $R^2$ and $R^3$ are as defined above.

The oxazolineazetidinone derivative of the formula (1) prepared by the process of this invention is useful as the intermediate for synthesizing cephalosporin-type antibiotics.

Processes for preparing the oxazolineazetidinone derivative of the formula (1) from the penicillin derivative of the formula (2) have been heretofore proposed. For example, S. Uyeo et al reported in J. Am. Chem. Soc., 101, 4403 (1979) a process in which chlorine and then a base (NaOH-Bu$_4$NCl) are permitted to act on a penicillin derivative of the formula (2) wherein $R^1$ is benzyl, $R^2$ is benzyloxycarbonyl and $R^3$ is hydrogen, thereby producing the corresponding oxazolineazetidinone derivative of the formula (1) in 60% yield. In J. Chem. Soc. (C) 3540 (1971), D. H. R. Barton et al proposed a process in which iodobenzene dichloride is allowed to act on a penicillin derivative of the formula (2) (wherein $R^1$ is benzyl, $R^2$ is methoxycarbonyl and $R^3$ is hydrogen) in a water-containing pyridine, thereby giving the corresponding oxazolineazetidinone derivative of the formula (1) in 18% yield. J. Stoodley et al taught in J. Chem. Soc., Perkin I, 181 (1978) a process in which mercury acetate

is reacted with penicillin G.

It is an object of the present invention to provide an improved process for preparing the oxazolineazetidinone derivative of the formula (1) from the penicillin derivative of the formula (2).

It is another object of this invention to provide a process for preparing the oxazolineazetidinone derivative of the formula (1) from the penicillin derivative of the formula (2) in high yields.

It is a further object of the invention to provide a process for preparing the derivative of the formula (1) from the derivative of the formula (2) with ease and high efficiency by a simple procedure without using any special reactant which requires careful handling.

It is a still further object of the invention to provide a process for preparing the derivative of the formula (1) from the derivative of the formula (2) without producing waste or other by-products to be disposed of.

These objects and other features of this invention will become apparent from the following description.

According to this invention, the oxazolineazetidinone derivative of the formula (1) is prepared by electrolyzing the penicillin derivative of the formula (2) in an alcoholic solvent in the presence of a chloride.

We have found that the process of this invention eliminates the drawbacks of conventional processes. The known processes suffer the serious defect of being unable to produce the contemplated compound in high yields and also present other problems including the use of reactants, such as chlorine or murcury acetate in stoichiometric or excess amounts which require careful handling. The use thereof involves the need of pyridine, potassium hydroxide or like base in large amounts acting on the reaction system in the course of the reaction or the post-treatment, thereby giving a great quantity of waste or other by-products. This entails a complicated procedure for reaction and difficulties in isolating and purifying the resulting product and in disposal of the waste. On the other hand, the process of this invention enables the production of the contemplated compound in high yields with ease and efficiency by a simple procedure without use of any special reactants requiring careful handling, facilitates the isolation and purification of the compound and produces no waste to be disposed of. Therefore, the present process is extremely advantageous over the prior art processes in that the former is capable of producing oxazolineazetidinone derivatives of the formula (1) in commercially favored manner.

Any suitable known compounds are usable as the starting material in the present process, namely the penicillin derivative of the formula (2). These compounds can be prepared in the usual manner from penicillin G, penicillin V or the like which is easily produced by usual fermentation method.

Examples of the groups represented by $R^1$ in the starting material of the formula (2) are as follows: the alkyl groups include alkyl groups having 1 to 10 carbon atoms such as methyl, ethyl, propyl, isopropyl, butyl, hexyl, octyl, and like groups; the alkenyl groups include alkenyl groups having 1 to 10 carbon atoms such as vinyl, allyl, isopropenyl, butenyl, hexenyl and like groups; the substituted or unsubstituted aralkyl groups include unsubstituted aralkyl group having 7 to 15 carbon atoms such as benzyl, phenetyl, etc. and aralkyl groups substituted with halogen atom, lower alkoxy group, nitro group, lower alkyl group or the like on the benzene ring; the substituted or unsubstituted aryl groups include phenyl groups optionally substituted with halogen atom, lower alkoxy group, nitro group, lower alkyl group or the like on the benzene ring such as phenyl, methylphenyl, nitrophenyl, chlorophenyl, methoxyphenyl, xylyl, etc.; the substituted or unsubstituted aryloxymethyl groups include aryloxymethyl groups optionally substituted with halogen atom, lower alkoxy group, nitro group, lower alkyl group or the like on the benzene ring such as phenoxymethyl, tolyloxymethyl, xylyloxymethyl, chlorophenoxymethyl, methoxyphenoxymethyl, nitrophenoxymethyl, etc.

Examples of the protected carboxyl groups represented by $R^2$ in the formula (2) are ester of the formula —COOR' (wherein R' represents methyl, ethyl and like lower alkyl groups; diphenylmethyl, triphenylethyl, o-methoxybenzyl, p-methoxybenzyl, p-chlorobenzyl, p-nitrobenzyl, benzyl and like alkyl groups replaced by substituted or unsubstituted aryl groups; or 2-chloroethyl, 2,2,2-trichloroethyl and like lower alkyl groups substituted with halogen atom), acid halide of the formula —COX (wherein X represents chlorine, bromine and like halogen atoms), acid amide of the formula —CONHR'' (wherein R'' represents hydrogen atom, lower alkyl group or substituted phenyl group), etc. The term "lower" prefixed to the words alkyl and alkoxy appearing above is used to mean that these groups have 1 to 5 carbon atoms.

$R^3$ in the formula (2) represents hydrogen atom or methoxy group.

The process of this invention is characterized by the step of electrolyzing the penicillin derivative of the formula (2) in an alcoholic solvent in the presence of a chloride. Alcoholic solvents useful in this electrolytic reaction are methanol, ethanol, isopropanol, tert-butyl alcohol and like alcohols. The alcohols may be used singly or in mixture. Also usable as the solvent is a mix of alcohol(s) with any other suitable solvent usually used. Preferred solvent is methanol or a mixed solvent predominantly containing methanol. Examples of solvents useful as components of mixed solvent are tert-butyl alcohol, tert-amyl alcohol and like alcohols other than methanol; tetrahydrofuran, dioxane, dimethylether, dimethoxyethane and like ethers; dichloromethane, chloroform, 1,2-dichloroethane, and like hydrocarbon halides; ethyl acetate, butyl acetate, methyl formate, and like esters, dimethylformamide, dimethylacetamide and like amides; acetonitrile, butyronitrile and like nitriles, etc. The proportions of the solvent and methanol forming the mixed solvent, although variable depending on a specific end product, preferably range from 10:1 to 1:10 (v/v). The alcoholic solvent is used in an amount of about 0.3 to 50 ml, preferably about 1 to 10 ml, per m mol of the substrate, although the amount is not limitative.

Examples of chlorides to be incorporated in the reaction system are alkali metal chlorides such as lithium chloride, sodium chloride, potassium chloride; alkaline earth metal chlorides such as magnesium chloride, barium chloride, calcium chloride; and copper chlorides, etc. Among them, LiCl, $MgCl_2$ or the like is particularly preferred. The amount of the chloride usually ranges from 0.1 w/v % to an amount sufficient to make a saturated solution, preferably from about 0.1 to 1 w/v %.

The electrolytic reaction of this invention can be conducted by using electrodes usually used, preferably those of platinum or carbon, under such conditions that ion of chlorine is discharged. According to this invention, electrolysis with current density maintained at a constant level is preferred to simplify the procedure for reaction. The current density involved, although variable depending on the shape of the electrolytic cell, is in the range of usually 1 to 500 mA/cm$^2$, preferably 2 to 50 mA/cm$^2$. Current is applied at an electric charge of about 2 to about 5 F, although it is variable with the particular substrate and other reaction conditions. The temperature ranges from about $-100°$ to about 50° C., favorably from about $-78°$ to about 30° C., although varying with the materials as used, the structure of the end product, etc. The electrolytic cell is of the undivided type having no diaphragm, though particularly not limited. The contemplated reaction is feasible by either a batchwise electrolysis or flow-cell electrolysis.

The oxazolineazetidinone derivative of the formula (1) thus obtained can be easily separated from the reaction mixture and purified by the usual method of separation such as solvent extraction, column chromatography, etc.

The present invention will be described hereinafter with reference to examples but is limited thereto in no way.

EXAMPLE 1

Synthesis of (1S, 5R)-6-(1-methoxycarbonyl-2-methyl-1-propenyl)-3-benzyl-4-oxa-2,6-diazabicyclo-[3.2.0]hept-2-en-7-one A 8 mg quantity of lithium chloride was dissolved in a mixture of 2 ml of methanol and 0.5 ml of tert-butyl alcohol. To the solution was added 66 mg of methyl ester of penicillin G to prepare an electrolyte. Electrolysis was continued for 90 minutes at a temperature of less than $-70°$ C. and at 13 V and an electric charge of 3 F while dipping platinum electrodes (1 cm$^2$) into the electrolyte and passing constant current of 10 mA through the electrolyte. Thereafter, the reaction mixture was stirred at $-20°$ C. for about 30 minutes and was extracted with chloroform. The extract was washed with water and dried over anhydrous sodium sulfate. The solvent was removed, and 65 mg of a light yellow liquid was obtained. The liquid was subjected to silica gel column chromatography using a 5:1 benzene-ethyl acetate mixture as the developer, giving 56 mg of contemplated compound in 92% yield. The results of instrumental analyses are as follows.

IR: 1780, 1720, 1640 cm$^{-1}$

NMR (CDCl$_3$): δ ppm = 1.54 and 2.20 (each 3H, s), 3.70 (2H, s), 3.72 (3H, s), 5.17 (1H, d, J=4 Hz), 5.94 (1H, d, J=4 Hz), 7.26 (5H, s), $[\alpha]_D^{18} = +43°$ (0.5%, CHCl$_3$)

EXAMPLE 2

Synthesis of (1S, 5R)-6-(1-methoxycarbonyl-2-methyl-1-propenyl)-3-benzyl-4-oxa-2,6-diazabicyclo-[3.2.0]hept-2-en-7-one Magnesium chloride (36 mg) was dissolved in a mixture of 2.5 ml of methanol and 0.5 ml of tertbutyl alcohol. To the solution was added 53 mg of methyl ester of penicillin G to prepare an electrolyte. With platinum electrodes (1 cm$^2$) dipped into the electrolyte, electrolysis was continued for 150 minutes (about 6 F) at a temperature of less than 0° C. and 3 to 8 V by applying constant current of 10 mA. Thereafter, the reaction mixture was stirred for about 30 minutes and extracted with chloroform. The extract was treated in the same manner as in Example 1, giving 41 mg of contemplated compound in 87% yield. The results of instrumental analyses were found identical with those of Example 1.

EXAMPLE 3

Synthesis of (1S, 5R)-6-(1-benzyloxycarbonyl-2-methyl-1-propenyl)-3-benzyl-4-oxa-2,6-diazabicyclo-[3.2.0]hept-2-en-7-one A 6.2 mg quantity of lithium chloride was dissolved in a mixture of 2 ml of methanol and 0.5 ml of tert-butyl alcohol. To the solution was added 62.4 mg of benzyl ester of penicillin G to prepare an electrolyte. The electrolyte was subjected to electrolysis under the same conditions as in Example 1. The isolation and purification gives 50 mg of contemplated compound in 88% yield.

The compound thus obtained was found to have the following physico-chemical properties.

IR: 1780, 1725, 1640 cm$^{-1}$

NMR (CDCl$_3$): δ ppm=1.41 and 2.07 (each 3H, s), 3.46 (2H, s), 4.90 (1H, d, J=4 Hz), 5.00 (2H, s), 5.67 (1H, d, J=4 Hz), 7.03 and 7.10 (each 5H, s).

EXAMPLE 4

Synthesis of (1S, 5R)-6-[1-(2,2,2-trichloroethoxy)carbonyl-2-methyl-1-propenyl]-3-benzyl-4-oxa-2,6-diazabicyclo[3.2.0]hept-2-en-7-one A 6.7 mg quantity of lithium chloride was dissolved in a mixture of 2 ml of methanol and 0.5 ml of tert-butyl alcohol. To the solution was added 72 mg of 2,2,2-trichloroethyl ester of penicillin G to prepare an electrolyte. The electrolyte was subjected to electrolysis under the same conditions as in Example 1, and the resulting reaction mixture was treated in the same manner as in Example 1 for separation and purification, giving 50 mg of contemplated compound in 75% yield.

The compound thus obtained was found to have the following physico-chemical properties.

IR: 1780, 1725, 1660, 1640 cm$^{-1}$

NMR (CDCl$_3$): δ ppm=1.42 and 2.06 (each 3H, s), 3.53 (2H, s), 4.60 (2H, s), 5.01 (1H, d, J=4 Hz), 5.77 (1H, d, J=4 Hz), 7.07 (5H, s).

EXAMPLE 5

Synthesis of (1S, 5R)-6-(1-methoxycarbonyl-2-methyl-1-propenyl)-3-phenoxymethyl-4-oxa-2,6-diazabicyclo[3.2.0]hept-2-en-7-one Lithium chloride (6.7 mg) was dissolved in a mixture of 2 ml of methanol and 0.5 ml of tert-butyl alcohol. Thereto was added 72 mg of methyl ester of penicillin V to prepare an electrolyte. Electrolysis was performed at a temperature of less than −70° C. and 10 to 15 V for 160 minutes (5 F) by dipping platinum electrodes (1 cm$^2$) in the electrolyte and passing constant current of 10 mA through the electrolyte. Thereafter, the reaction mixture was stirred at less than −10° C. for about 30 minutes and extracted with ethyl acetate. The extract was treated in the same manner as in Example 1, affording 53 mg of contemplated compound in 80% yield.

The compound was found to have the following physico-chemical properties.

IR: 1780, 1730, 1690, 1600 cm$^{-1}$

NMR (CDCl$_3$): δ ppm=1.73 and 2.13 (each 3H, s), 3.62 (3H, s), 4.60 (2H, s), 5.10 (1H, d, J=4 Hz), 5.87 (1H, d, J=4 Hz), 6.5–7.3 (5H, m).

EXAMPLE 6

Synthesis of (1S, 5R)-6-(1-methoxycarbonyl-2-methyl-1-propenyl)-1-methoxy-3-benzyl-4-oxa-2,6-diazabicyclo[3.2.0]hept-2-en-7-one A 39 mg quantity of methyl ester of 6-methoxy-6-phenylacetamide penicillanic acid and 10 mg of anhydrous magnesium chloride were dissolved in a mixture of 2.5 ml of methanol and 0.5 ml of tetrahydrofuran to prepare an electrolyte. The electrolyte was placed in an electrolytic cell into which platinum electrodes were dipped. Electrolysis was carried out by passing constant current of 10 mA through the electrolyte at room temperature and 3.5 to 4.5 V for 85 minutes (5 F). Thereafter, the reaction mixture was extracted with ethyl acetate. The extract was treated in the same manner as in Example 1, giving 30 mg of contemplated compound in 85% yield.

The compound thus obtained was found to have the following physico-chemical properties.

IR: 1790, 1730, 1650 cm$^{-1}$

NMR (CDCl$_3$): δ ppm=1.32 (3H, s), 2.05 (3H, s), 3.45 (3H, s), 3.57 (5H, s), 5.71 (1H, s), 7.10 (5H, s).

EXAMPLE 7

Synthesis of (1S, 5R)-6-(1-p-nitrobenzyloxycarbonyl-2-methyl-1-propenyl)-1-methoxy-3-benzyl-4-oxa-2,6-diazabicyclo[3.2.0]hept-2-en-7-one An electrolyte was prepared by dissolving 50 mg of p-nitrophenylmethyl ester of 6-methoxy-6-phenylacetamide penicillanic acid and 10 mg of anhydrous magnesium chloride in a mixture of 2.5 ml of methanol and 0.5 ml of tetrahydrofuran. Electrolysis was conducted under same conditions as in Example 6, and the resulting reaction mixture was treated in the same manner as in Example 6, giving 31 mg of contemplated compound. Yield 67%.

The compound thus obtained was found to have the following physico-chemical properties.

IR: 1790, 1735, 1650, 1530 cm$^{-1}$

NMR (CDCl$_3$): δ ppm=1.35 (3H, s), 2.06 (3H, s), 3.38 (3H, s), 3.50 (2H, s), 5.05 (2H, s), 5.59 (1H, s), 7.03 (5H, s), 7.62 (4H, ABq).

EXAMPLE 8

Synthesis of (1S, 5R)-6-(1-methoxycarbonyl-2-methyl-1-propenyl)-1-methoxy-3-phenoxymethyl-4-oxa-2,6-diazabicyclo[3,2,0]hept-2-en-7-one An electrolyte was prepared by dissolving 40 mg of methyl ester of 6-methoxy-6-phenoxyacetamide penicillanic acid and 10 mg of anhydrous magnesium chloride in a mixture of 2.5 ml of methanol and 0.5 ml of tetrahydrofuran. Electrolysis was conducted under the same conditions as in Example 6, giving 30 mg of contemplated compound in 83% yield.

The compound thus obtained was found to have the following physico-chemical properties.

IR: 1780, 1735, 1640 cm$^{-1}$

NMR (CDCl$_3$): δ ppm=1.67 and 2.69 (6H, s), 3.44 (3H, s), 3.59 (3H, s), 4.62 (2H, s), 5.77 (1H, s), 6.6–7.3 (5H, m).

EXAMPLE 9

Synthesis of (1S, 5R)-6-(1-methoxycarbonyl-2-methyl-1-propenyl)-3-benzyl-4-oxa-2,6-diazabicyclo-[3.2.0]hept-2-en-7-one A procedure similar to that of Example 2 was repeated by using 53 mg of methyl ester of 6-epipenicillin G giving 40 mg of contemplated compound. Yield 85%.

The compound thus obtained was found to have the following physico-chemical properties.

The results identical with those of Example 1 were obtained by IR and NMR $[\alpha]_D^{20} = -45°$ (0.5%, CHCl$_3$)

We claim:

1. A process for preparing an oxazolineazetidinone derivative represented by the formula (1)

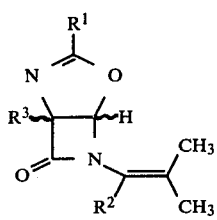  (1)

wherein R$^1$ represents hydrogen atom, alkyl group, alkenyl group, substituted or unsubstituted aralkyl group, substituted or unsubstituted aryl group, or substituted or unsubstituted aryloxymethyl group, R$^2$ represents free or protected carboxyl group and R$^3$ represents hydrogen atom or methoxy group, the process comprising electrolyzing a penicillin derivative represented by the formula (2)

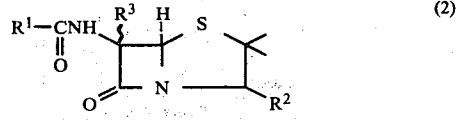  (2)

wherein R$^1$, R$^2$ and R$^3$ are as defined above in an alcoholic solvent in the presence of a chloride.

2. A process as defined in claim 1 in which a penicillin derivative of the formula (2) is used in which R$^1$ is phenyl, phenoxy, benzyl or phenoxymethyl.

3. A process as defined in claim 1 in which a penicillin derivative of the formula (2) is used in which R$^2$ is ester group of the formula —COOR′ wherein R′ is lower alkyl, lower alkyl replaced by substituted or unsubstituted aryl or lower alkyl substituted with halogen.

4. A process as defined in claim 1 in which the alcoholic solvent is methanol or a mixed solvent predominantly containing methanol.

5. A process as defined in claim 4 in which the mixed solvent contains methanol predominantly is methanol-tert-butyl alcohol or methanol-tetrahydrofuran.

6. A process as defined in claim 1 in which the chloride is alkali metal chloride or alkaline earth metal chloride.

7. A process as defined in claim 6 in which the chloride is lithium chloride or magnesium chloride.

8. A process as defined in claim 1 in which the electrolysis is conducted at a constant current.

9. A process as defined in claim 8 in which the electrolysis is carried out at a current density of 1 to 500 mA/cm$^2$.

10. A process as claimed in claim 8 in which the electrolysis is performed at a temperature of about −100° to about 50° C.

* * * * *

UNITED STATES PATENT AND TRADEMARK OFFICE
CERTIFICATE OF CORRECTION

PATENT NO. : 4,379,032

DATED : April 5, 1983

INVENTOR(S) : TORII, ET AL.

It is certified that error appears in the above-identified patent and that said Letters Patent is hereby corrected as shown below:

Title page: item [30] should be added as follows:

-- [30]  FOREIGN APPLICATION PRIORITY DATA

August 25, 1981 [JP] Japan . . . . . . . . . . 133775 --

Signed and Sealed this

Twelfth Day of April, 1988

*Attest:*

DONALD J. QUIGG

*Attesting Officer*  *Commissioner of Patents and Trademarks*